(12) United States Patent
Long (10) Patent No.: US 11,517,052 B2
(45) Date of Patent: Dec. 6, 2022

(54) INTELLIGENT INDUCTION ATOMIZER

(71) Applicant: Shenzhen Yongtu Technology Co., Ltd., Shenzhen (CN)

(72) Inventor: Biao Long, Shenzhen (CN)

( * ) Notice: Subject to any disclaimer, the term of this patent is extended or adjusted under 35 U.S.C. 154(b) by 324 days.

(21) Appl. No.: 16/935,225

(22) Filed: Jul. 22, 2020

(65) Prior Publication Data

US 2020/0345077 A1    Nov. 5, 2020

(51) Int. Cl.
*A24F 40/57* (2020.01)
*A24F 40/42* (2020.01)
*A24F 40/51* (2020.01)
*A24F 40/465* (2020.01)
*A24F 13/00* (2006.01)

(52) U.S. Cl.
CPC ............ *A24F 40/57* (2020.01); *A24F 40/42* (2020.01); *A24F 40/465* (2020.01); *A24F 40/51* (2020.01)

(58) Field of Classification Search
CPC ...................................................... A24F 47/00
USPC .................................................. 131/328–329
See application file for complete search history.

(56) References Cited

U.S. PATENT DOCUMENTS

| 2,253,071 | A | * | 8/1941 | Gordon | ............... B05B 7/2429 239/351 |
| 2,514,751 | A | * | 7/1950 | Engstrum | ............... B05B 11/06 239/357 |
| 2020/0305559 | A1 | * | 10/2020 | Eberra | ............... A44C 15/002 |

* cited by examiner

*Primary Examiner* — Phuong K Dinh (57) ABSTRACT

An intelligent induction atomizer comprises a main shell and a bottom shell detachably mounted at the lower end of the main shell. A bottle container, a middle baffle and a control mainboard are arranged in the main shell. The atomizer can be used for sterilization by means of infrared inductive atomization, and adopts the battery to supply power, thereby being convenient and safe to use; and multiple purposes can be fulfilled by adding or changing liquid in the bottle container.

10 Claims, 7 Drawing Sheets

INTELLIGENT INDUCTION ATOMIZER

BACKGROUND OF THE INVENTION

1. Technical Field

The utility model relates to the technical field of daily necessities, in particular to an intelligent induction atomizer.

2. Description of Related Art

To prevent and reduce the breeding and spreading of epidemical bacteria and viruses, regular sterilization is necessary for most public places, and particularly when an infectious disease prevails, the entrance and exit of all public places such as border checkpoints, transportation hubs, hospitals, abattoirs, food processing factories, schools, villages and farms should be sterilized incessantly. At present, sterilization is generally performed manually by means of a sprayer, which brings a heavy workload and high labor and time consumption and may result in resource waste due to high randomness. In hot summer, people adopt mosquito dispellers to dispel or kill mosquitoes to prevent against mosquito infestation. Nowadays, anti-mosquito products commonly used in life include mosquito incense coils, mosquito-repellent mats, electric mosquito repellent mats, electric mosquito repellent liquor, and the like, wherein the mosquito incense coils and the mosquito-repellent mats should be burnt with an open fire to release smoke to repel mosquitoes, thus being neither safe nor environmentally friendly; and the electric mosquito repellent mats and electric mosquito repellent liquor should be always kept in a power-on state in use, may cause electric shocks when plugged, and are neither energy-efficient nor portable.

BRIEF SUMMARY OF THE INVENTION

The objective of the utility model is to provide an intelligent induction atomizer to overcome the abovementioned shortcomings of the prior art.

To fulfill the aforesaid objective, the utility model adopts the following technical solution:

An intelligent induction atomizer comprises a main shell and a bottom shell detachably mounted at the lower end of the main shell, wherein a bottle container, a middle baffle and a control mainboard are arranged in the main shell, the middle baffle is provided with a thread groove and a battery case, a thread tapped on an opening of the bottle container is fastened in the thread groove, a battery is mounted in the battery case, a suction rod is arranged in the bottle container, a fixed tube is mounted in the thread groove, an, atomization piece is arranged at the upper end of the fixed tube, the top end of the suction rod is disposed in the fixed tube and contacts with the atomization piece, a fixed seat is further arranged in the main shell, the fixed tube is disposed in the fixed seat, the main shell is formed with an atomization air vent which is located exactly opposite to the atomization piece, the battery and the atomization piece are electrically connected to the control mainboard, an infrared induction lamp is integrated on the control mainboard, and the main shell is formed with two through holes which are located over the infrared induction lamp.

Preferably, the lower end of the suction rod is sleeved with a tube, wherein the lower end of the tube is sealed, the upper end of the tube is connected with the fixed tube, a water inlet is formed in the lateral side of the tube, and a spring is arranged between the inner bottom surface of the tube and the bottom of the suction rod.

Preferably, the tube is provided with a cover plate which is located at the opening of the bottle container, and the opening of the bottle container is sealed by the cover plate.

Preferably, a first waterproof rubber washer is arranged at the joint of the tube and the fixed tube, a second waterproof rubber washer is arranged in the fixed seat, and the atomization piece is disposed in an inner ring of the second waterproof rubber washer.

Preferably, the battery is a rechargeable battery, and a USB interface is arranged on the main shell and is electrically connected to the control mainboard.

Preferably, a switch button is arranged outside the main shell and is connected to the control mainboard.

Preferably, the control mainboard is integrated with a main control chip and a drive circuit, wherein the switch button and the USB interface are electrically connected to the main control chip, and a PWM output terminal of the main control chip is connected to the drive circuit; and the drive circuit comprises an MOS transistor and an induction coil, wherein a gate of the MOS transistor is grounded through a sixth resistor and is connected to the main control chip through a second resistor, a drain of the MOS transistor is connected to the induction coil, and the induction coil is connected to the atomization piece through a sixth capacitor.

Preferably, the infrared induction lamp comprises an infrared transmitting circuit and an infrared receiving circuit, and a WL output terminal of the main control chip is connected to the infrared transmitting circuit which comprises a first resistor, a seventh resistor, a tenth resistor, an infrared transmitting diode and a triode, wherein one terminal of the first resistor is connected to the WL output terminal and one terminal of the tenth resistor, the other terminal of the first resistor is connected to a base of the triode, the other terminal of the tenth resistor is grounded, a collector of the triode is connected to one terminal of the seventh resistor, an emitter of the triode is grounded, the other terminal of the seventh resistor is connected to a cathode of the infrared transmitting diode, and an anode of the infrared transmitting diode is connected to a ninth terminal of the main control chip.

Preferably, an IR-IN input terminal of the main control chip is connected to the infrared receiving circuit which comprises an infrared reflective sensor, a seventeenth resistor, a nineteenth resistor, a seventh capacitor and an eighth capacitor, wherein the IR-IN input terminal of the main control chip is connected to a first terminal of the infrared reflective sensor and one terminal of the nineteenth resistor, a second terminal of the infrared reflective sensor is grounded, and a third terminal of the infrared reflective sensor is grounded through the seventh capacitor and the eighth capacitor and is connected to the ninth terminal of the main control chip through the seventeenth resistor.

Preferably, a finger site is arranged on the outer side of the bottom shell.

By adoption of the above technical solution, the utility model has the following advantages:

1. Liquid is sucked out of the bottle container by the suction rod and is then atomized by the atomization piece, and the atomized liquid is discharged, so that the purpose of sterilization is realized by means of atomizing diffusion;

2. The internal battery is used as a power supply, so that the atomizer can operate normally without external power and thus can be used on various occasions, constraints and limitations of wired power supply are eliminated, and potential safety hazards caused by repeated plugging and unplugging can be eliminated.

3. An external object signal can be detected by the infrared induction lamp and can be fed back to the main control chip, which in turn sends an, instruction to the atomization piece to enable the atomization piece to spray mist, so that the entire atomizer is more intelligent; and 4. The bottom shell can be removed, and the bottle container fastened to the thread groove through the thread can be dismantled, so that liquid in the bottle container can be added or changed to realize different effects, such as humidification, aromatherapy and mosquito repelling.

DETAILED DESCRIPTION OF THE INVENTION

The embodiments of the utility model are expounded below in conjunction with the accompanying drawings. Clearly, the utility model may be implemented in different ways defined and covered by the claims.

As shown in FIG. 1 to FIG. 8, this embodiment provides an intelligent induction atomizer which comprises a main shell 1 and a bottom shell 2 detachably mounted at the lower end of the main shell 1, wherein a bottle container 3, a middle baffle 4 and a control mainboard 5 are arranged in the main shell 1, the middle baffle 4 is provided with a thread groove 6 and a battery case 7, a thread tapped on an opening of the bottle container 3 is fastened in the thread groove 6, a battery 8 is mounted in the battery case 7, a suction rod 9 is arranged in the bottle container 3, a fixed tube 10 is mounted in the thread groove 6, an atomization piece 11 is arranged at the upper end of the fixed tube 10, the top end of the suction rod 9 is disposed in the fixed tube 10 and contacts with the atomization piece 11, a fixed seat 12 is further arranged in the main shell 1, the fixed tube 10 is disposed in the fixed seat 12, the main shell 1 is formed with an atomization air vent 13 which is located exactly opposite to the atomization piece 11, the battery 8 and the atomization piece 11 are electrically connected to the control mainboard 5, an infrared induction lamp 22 is integrated on the control mainboard, and the main shell 1 is formed with two through holes 100 which are located over the infrared induction lamp 22.

In a preferred embodiment of the utility model, in specific operation, liquid is sucked out of the bottle container 3 by the suction rod 9 and is then atomized by the atomization piece 11, the atomized liquid is then discharged via the atomization air vent 13, the atomization piece is received in the fixed tube 10 and is connected with the suction rod 9, and the fixed tube 10 is fastened by the fixed seat 12, so that the overall structural stability is guaranteed; and internal power is supplied by the battery 8, so that the atomizer can operate normally without external power and thus can be used on various occasions, constraints and limitations of wired power supply are eliminated to ensure that the atomizer can be used more easily and conveniently during outdoor travel, and potential safety hazards caused by repeated, plugging and unplugging can be eliminated. In addition, the atomizer in this embodiment can be adjusted according to preferences and purposes. For example, the bottom shell 2 can be removed, and then the bottle container 3 can be dismantled to selectively add or change liquid in the bottle container. If water is added into the bottle container, a humidification effect can be realized. If a liquid mosquito repellent is added into the bottle container, a mosquito repelling and killing effect can be realized. If aromatic liquor is added into the bottle container, an air purification and sterilization effect can be realized. In this way, the atomizer can realize different effects and functions to be used in different fields.

Figure 1:
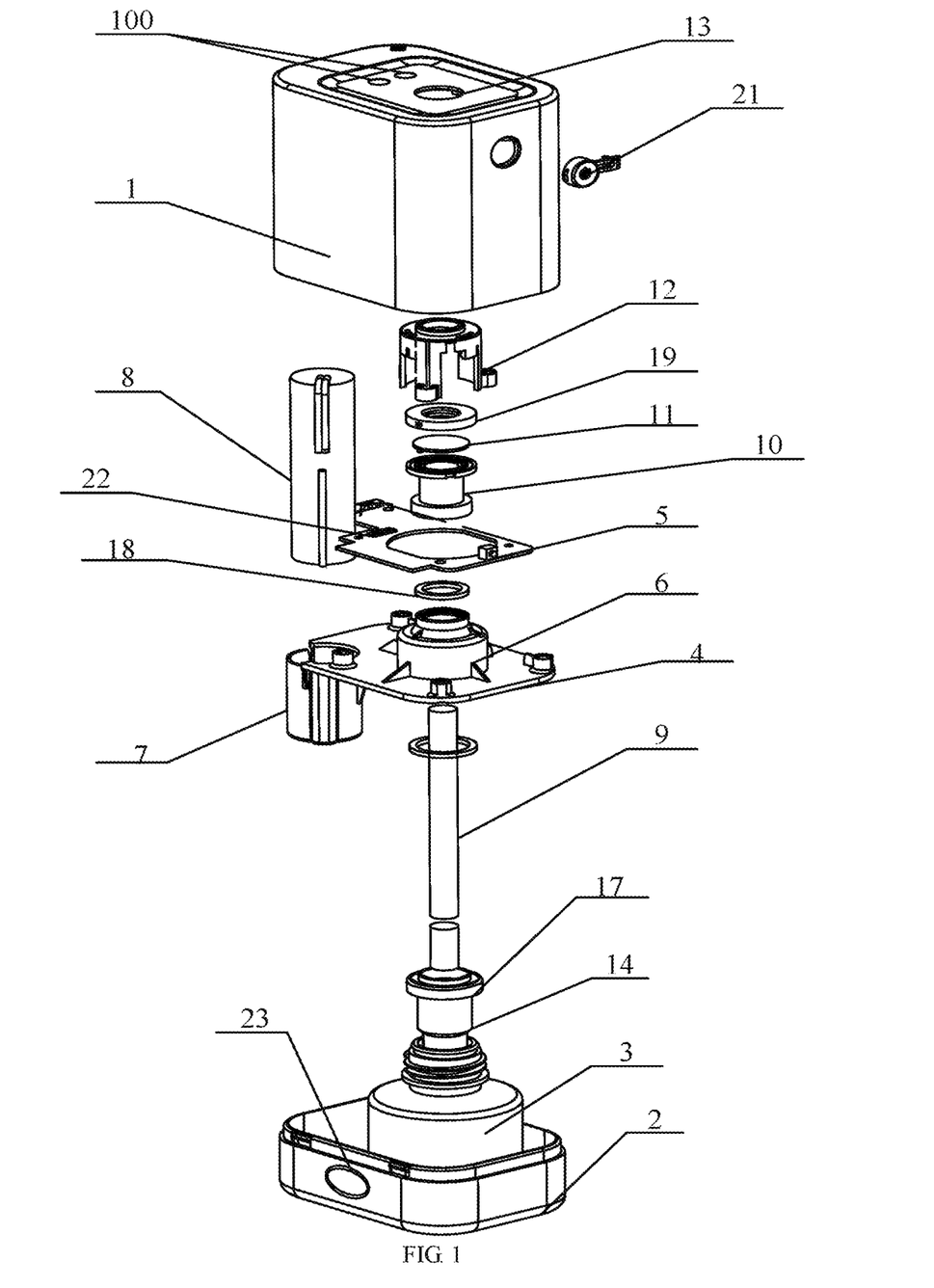
FIG. 1 is a structural principle diagram of an embodiment of the utility model.
Figure 2:
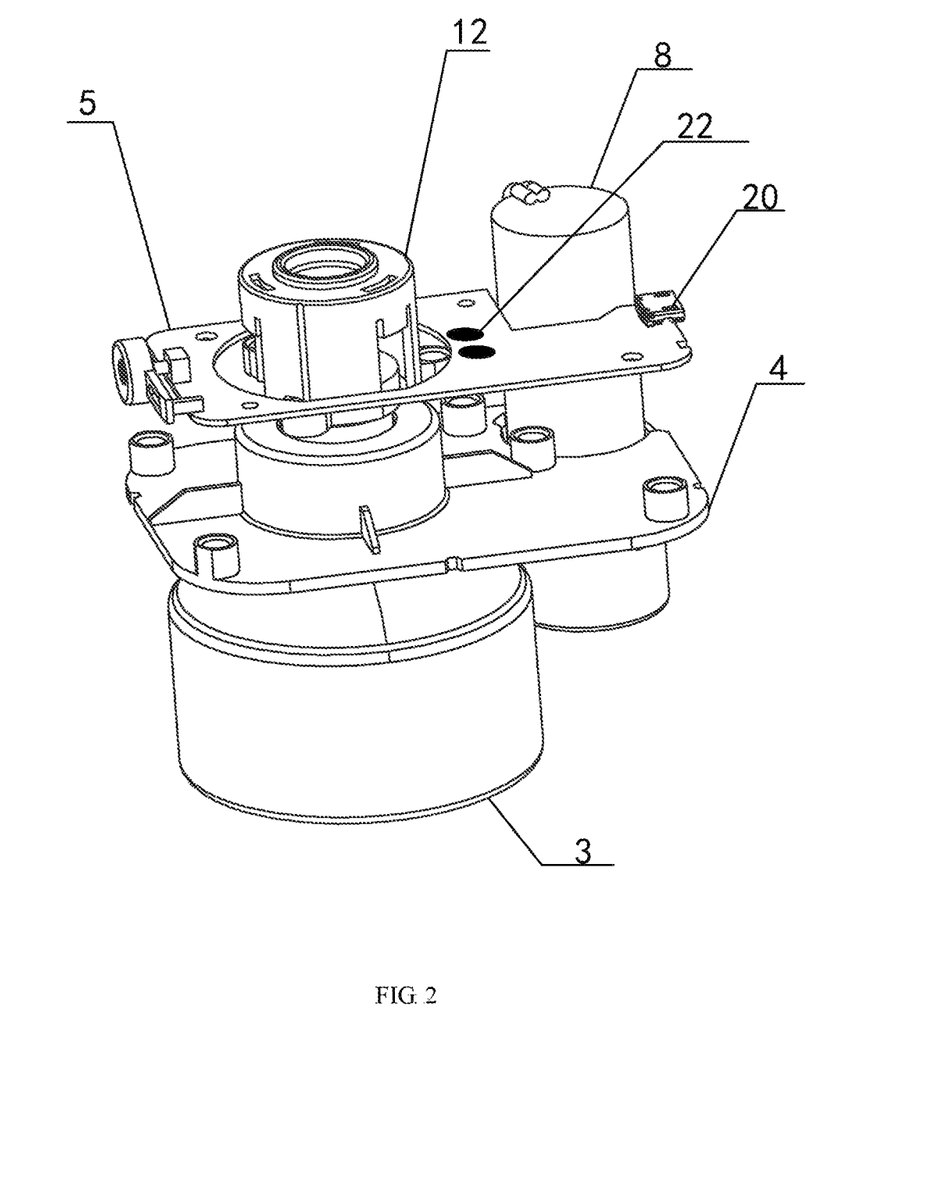
FIG. 2 is an internal structural diagram of the embodiment of the utility model.
Figure 3:
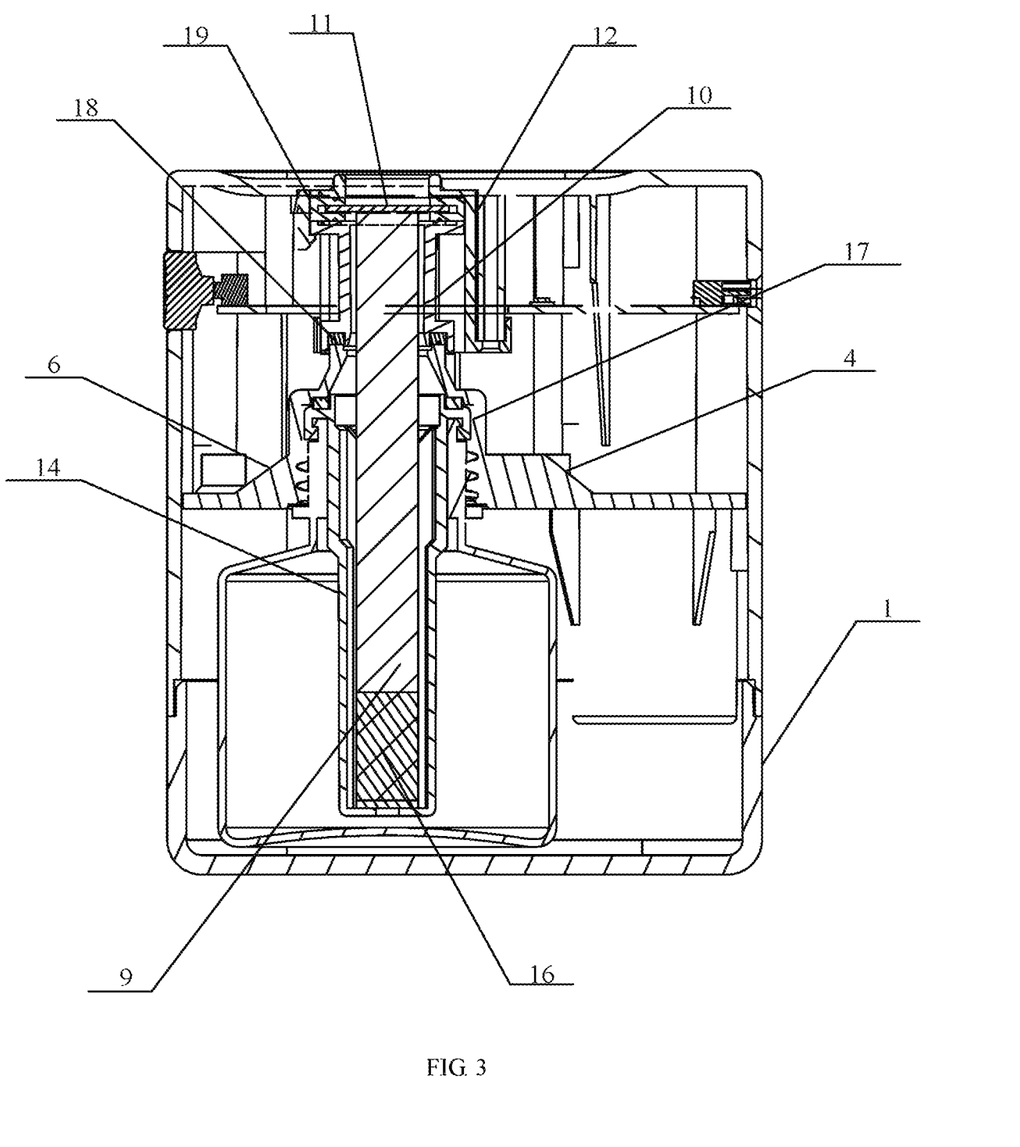
FIG. 3 is a sectional view of the embodiment of the utility model.

In a preferred embodiment of the utility model, to protect the suction rod 9 and guarantee incessant contact between the suction rod 9 and the atomization piece 11, the lower end of the suction rod 9 is sleeved with a tube 14, wherein the lower end of the tube 14 is sealed, the upper end of the tube 14 is connected with the fixed tube 10, a water inlet 15 is formed in the lateral side of the tube 14, and a spring 16 is arranged between the inner bottom surface of the tube 14 and the bottom of the suction rod 9. The suction rod 9 is sleeved with the tube 14, thus being kept stable and being prevented against contact with the outside; and the spring 16 abuts against the suction rod 9 to ensure that the suction rod 9 is always in contact with the atomization piece 11 to guarantee normal atomization.

In a preferred embodiment of the utility model, to seal the opening of the bottle container 3, the tube 14 is provided with a cover plate 17 which is located at the opening of the bottle container 3, and the opening of the bottle container 3 is sealed by the cover plate 17.

In a preferred embodiment of the utility model, to improve the anti-leakage effect of the atomization piece 11, a first waterproof rubber washer 18 is arranged at the joint of the tube 14 and the fixed tube 10, a second waterproof rubber washer 19 is arranged in the fixed, seat 12, and the atomization piece 11 is disposed in an inner ring of the second waterproof rubber washer 19.

Figure 4:
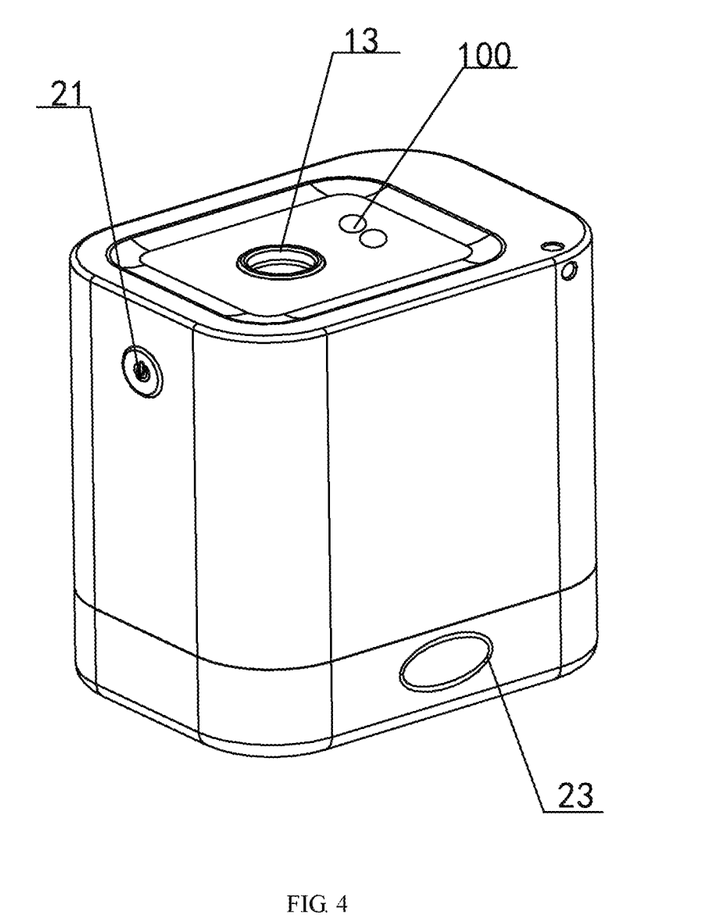
FIG. 4 is a perspective view of the embodiment of the utility model.

In a preferred embodiment of the utility model, the battery 8 is a rechargeable battery, and a USB interface 20 is arranged on the main shell 1 and is electrically connected to the control mainboard 5, so that the battery 8 can be used repeatedly to realize energy conservation and environmental friendliness, and does not need to be changed.

In a preferred embodiment of the utility model, a switch button 21 is arranged outside the main shell 1 and is connected to the control mainboard 5, and the atomizer can be controlled to start to operate or to stop by means of the switch button 21.

Figure 5:
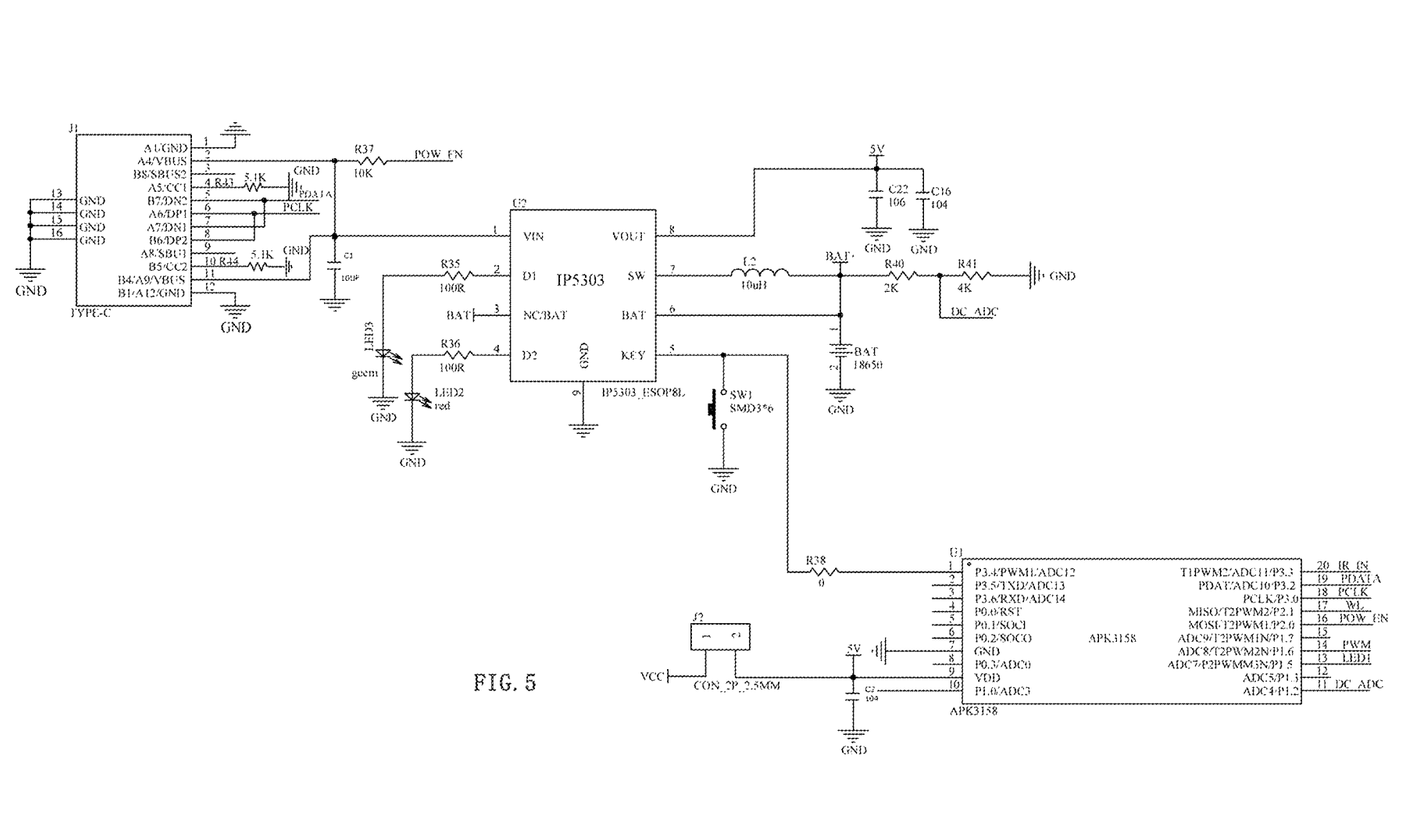
FIG. 5 is a circuit diagram of a main control chip of the embodiment of the utility model.
Figure 8:
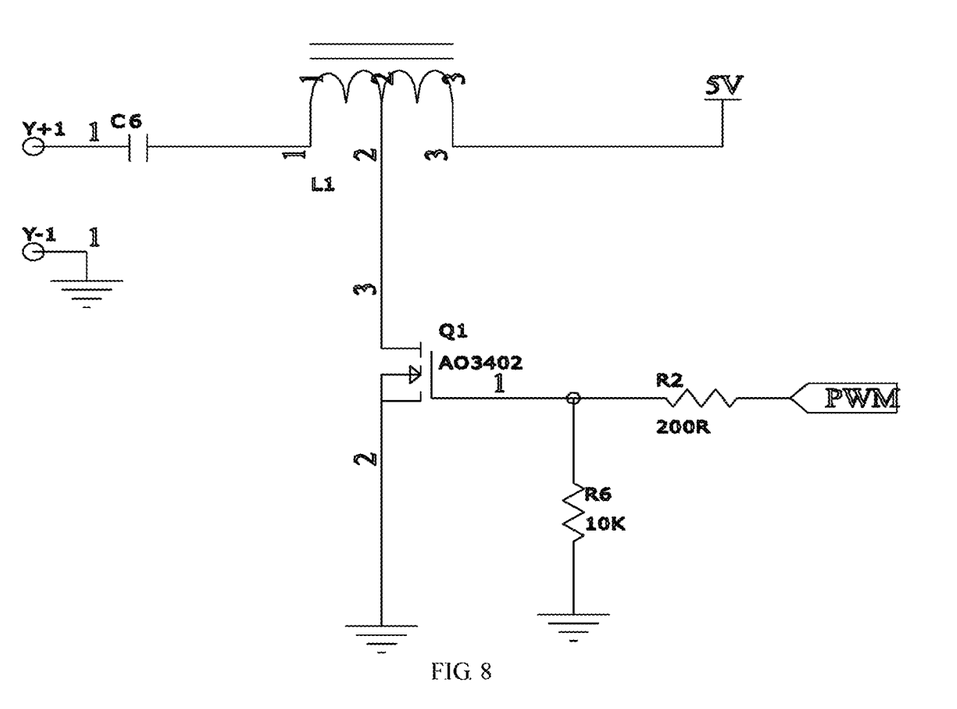
FIG. 8 is a circuit diagram of a drive circuit of the embodiment of the utility model.

In this embodiment, the control mainboard 5 is integrated with a main control chip U1 and a drive circuit, wherein the main control chip may be an APK3158 chip or other chips with the same function, the switch button 21 and the USB interface 20 are electrically connected to the main control chip U1, and a PWM output terminal of the main control chip U1 is connected to the drive circuit; and the drive circuit comprises an MOS transistor Q1 and an induction coil L1, wherein a gate of the MOS transistor Q1 is grounded through a sixth resistor R6 and is connected to the main control chip U1 through a second resistor R2, a drain of the MOS transistor Q1 is connected to the induction coil L1, the induction coil L1 is connected to the atomization piece 11 through a sixth capacitor C6, and the main control chip U1 receives an on signal from the switch button 21 and outputs a corresponding PWM pulse signal, which can effectively control the drive circuit to control the atomization piece 11 to operate.

Figure 6:
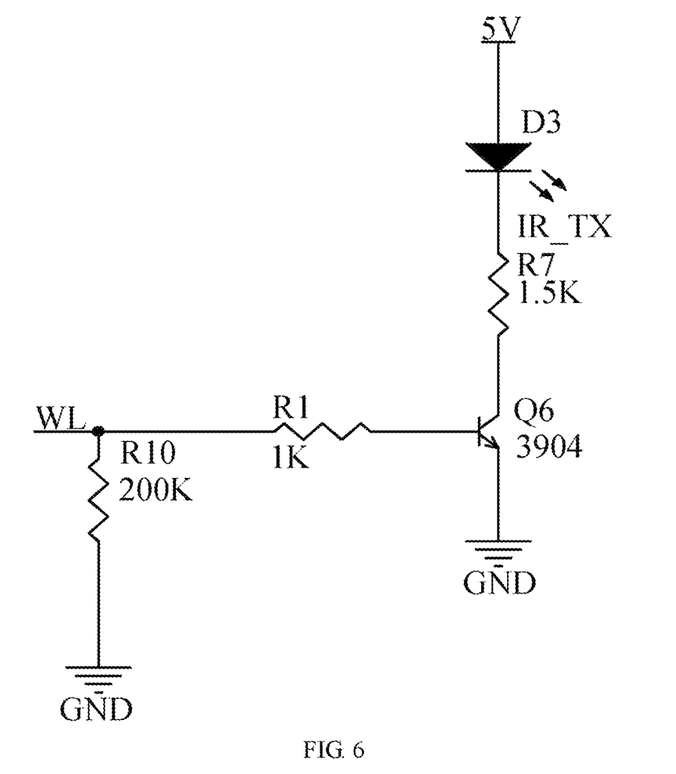
FIG. 6 is a circuit diagram of an infrared transmitting circuit of the embodiment of the utility model.

In a preferred embodiment of the utility model, the infrared induction lamp 22 comprises an infrared transmitting circuit and an infrared receiving circuit, and a WL output terminal of the main control chip U1 is connected to the infrared transmitting circuit which comprises a first resistor R1, a seventh resistor R7, a tenth resistor R10, an infrared transmitting diode D3 and a triode Q6, wherein one terminal of the first resistor R1 is connected to the WL output terminal and one terminal of the tenth resistor R10, the other terminal of the first resistor R1 is connected to a base of the triode Q6, the other terminal of the tenth resistor R10 is grounded, a collector of the triode Q6 is connected to one terminal of the seventh resistor R7, an emitter of the triode Q6 is grounded, the other terminal of the seventh resistor R7 is connected to a cathode of the infrared transmitting diode D3, and an anode of the infrared transmitting diode D3 is connected to an ninth terminal of the main control chip U1.

Figure 7:
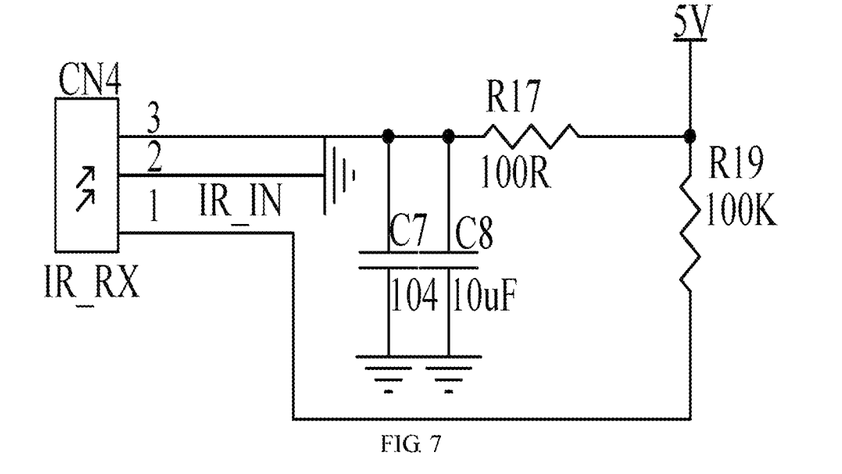
FIG. 7 is a circuit diagram of an infrared receiving circuit of the embodiment of the utility model.

In a preferred embodiment of the utility model, an IR-IN input terminal of the main control chip U1 is connected to the infrared receiving circuit which comprises an infrared reflective sensor CN4, a seventeenth resistor R17, a nineteenth resistor R19, a seventh capacitor C7 and an eighth capacitor C8, wherein the IR-IN input terminal of the main control chip U1 is connected to a first terminal of the infrared reflective sensor CN4 and one terminal of the nineteenth resistor R19, a second terminal of the infrared reflective sensor CN4 is grounded, a third terminal of the infrared reflective sensor CN4 is grounded through the seventh capacitor C7 and the eighth capacitor C8 and is connected to the ninth terminal of the main control chip U1 through the seventeenth resistor R17.

In a preferred embodiment of the utility model a finger site 23 is arranged on the outer side of the bottom shell 2, and a user can hold the bottom shell 2 by means of the finger site 23 so as to dismantle the bottom shell 2 easily.

The aforesaid embodiments are merely preferred ones of the utility model, and are not intended to limit the patent scope of the utility model. All equivalent structures or equivalent process transformations made on the basis of the contents in the description and accompanying drawings of the utility model, or direct or indirect applications to other relating technical fields should also fall within the patent protection scope of the utility model.

What is claimed is:

1. An intelligent induction atomizer, comprising a main shell and a bottom shell detachably mounted at a lower end of the main shell, wherein a bottle container, a middle baffle and a control mainboard are arranged in the main shell, the middle baffle is provided with a thread groove and a battery case, a thread tapped on an opening, of the bottle container is fastened in the thread groove, a battery is mounted in the battery case, a suction rod is arranged in the bottle container, a fixed tube is mounted in the thread groove, an atomization piece is arranged at an upper end of the fixed tube, a top end of the suction rod is disposed in the fixed tube and contacts with the atomization piece, a fixed seat is further arranged in the main shell, the fixed tube is disposed in the fixed seat, the main shell is formed with an atomization air vent which is located exactly opposite to the atomization piece, the battery and the atomization piece are electrically connected to the control mainboard, an infrared induction lamp is integrated on the control mainboard, and the main shell is formed with two through holes which are located over the infrared induction lamp.

2. The intelligent induction atomizer according to claim 1, wherein a lower end of the suction rod is sleeved with a tube, wherein a lower end of the tube is sealed, an upper end of the tube is connected with the fixed tube, a water inlet is formed in a lateral side of the tube, and a spring is arranged between an inner bottom surface of the tube and a bottom of the suction rod.

3. The intelligent induction atomizer according to claim 2, wherein the tube is provided with a cover plate which is located at the opening of the bottle container, and the opening of the bottle container is sealed by the cover plate.

4. The intelligent induction atomizer according to claim 3, wherein a first waterproof rubber washer is arranged at a joint of the tube and the fixed tube, a second waterproof rubber washer is arranged in the fixed seat, and the atomization piece is disposed in an inner ring of the second waterproof rubber washer.

5. The intelligent induction atomizer according to claim 1, wherein the battery is a rechargeable battery, and a USB interface is arranged on the main shell and is electrically connected to the control mainboard.

6. The intelligent induction atomizer according to claim 5, wherein a switch button is arranged, outside the main shell and is connected to the control mainboard.

7. The intelligent induction atomizer according to claim 6, wherein the control mainboard is integrated with a main control chip and a drive circuit, the switch button and the USB interface are electrically connected to the main control chip, and a PWM output terminal of the main control chip is connected to the drive circuit; and the drive circuit comprises an MOS transistor and an induction coil, wherein a gate of the MOS transistor is grounded through a sixth resistor and is connected to the main control chip through a second resistor, a drain of the MOS transistor is connected to the induction coil, and the induction coil is connected to the atomization piece through a sixth capacitor.

8. The intelligent induction atomizer according to claim 7, wherein the infrared induction lamp comprises an infrared transmitting circuit and an infrared receiving circuit, and, a WL output terminal of the main control chip is connected to the infrared transmitting circuit which comprises a first resistor, a seventh resistor, a tenth resistor, an infrared transmitting diode and a triode, wherein one terminal of the first resistor is connected to the WL output terminal and one terminal of the tenth resistor, another terminal of the first resistor is connected to a base of the triode, another terminal of the tenth resistor is grounded, a collector of the triode is connected to one terminal of the seventh resistor, an emitter of the triode is grounded, another terminal of the seventh resistor is connected to a cathode of the infrared transmitting diode, and an anode of the infrared transmitting diode is connected to a ninth terminal of the main control chip.

9. The intelligent induction atomizer according to claim 8, wherein an IR-IN input terminal of the main control chip is connected to the infrared receiving circuit which comprises an infrared reflective sensor, a seventeenth resistor, a nineteenth resistor, a seventh capacitor and an eighth capacitor, wherein the IR-IN input terminal of the main control chip is connected to a first terminal of the infrared reflective sensor and one terminal of the nineteenth resistor, a second terminal of the infrared reflective sensor is grounded, and a third terminal of the infrared reflective sensor is grounded through the seventh capacitor and the eighth capacitor and is connected to the ninth terminal of the main control chip through the seventeenth resistor.

10. The intelligent induction atomizer according to claim 1, wherein a finger site is arranged on an outer side of the bottom shell.

* * * * *